United States Patent [19]
Lubkin

[11] Patent Number: 6,096,733
[45] Date of Patent: Aug. 1, 2000

[54] DRUGS FOR TOPICAL APPLICATION OF SEX STEROIDS IN THE TREATMENT OF DRY EYE SYNDROME, AND METHODS OF PREPARATION AND APPLICATION

[75] Inventor: Virginia Lubkin, One Blackstone Pl., Bronx, N.Y. 10471

[73] Assignee: Virginia Lubkin, Brnx, N.Y.

[21] Appl. No.: 09/208,423

[22] Filed: Dec. 10, 1998

[51] Int. Cl.$^7$ ................................................. A61K 31/56
[52] U.S. Cl. ........................ 514/182; 514/169; 514/177; 514/178; 514/912; 514/914
[58] Field of Search .................... 514/182, 169, 514/177, 178, 912, 914

[56] References Cited

U.S. PATENT DOCUMENTS

| | | |
|---|---|---|
| 4,642,305 | 2/1987 | Johansson et al. . |
| 4,774,236 | 9/1988 | Cook et al. . |
| 4,861,763 | 8/1989 | Cook et al. . |
| 4,866,049 | 9/1989 | Maumenee et al. . |
| 5,041,434 | 8/1991 | Lubkin ..................................... 514/182 |

OTHER PUBLICATIONS

Ostrogen–Therapie in Keratokonjunktivitis Sicca, Dr. J. Akramian et al., Spektrum der Augenheilkunde (Spektrum Augenheilkd.) Nov. 5, 1997 (195–97).

Olige Estradio–Hemihydrat–Augentropfen 0.025 Prozent; Fischer, H and Reimann H., Neues Rezeptur–Formularium (NRF) Pharmazeutisches Laboratorium, Pharmazeutische Zeitung (Pharm. Ztg.) Jan. 14, 1999 144/2 (38–40).

Benitez del Castillo, J.M.E, et al., "ffects of Estrogen Use on Lens Transmittance in Postmenopausal Women," *Ophthalmology* 1997; 104:970–973.

Sator, M.O., et al., "Treatment of menopausal keratoconjunctivitis sicca with topical oestradiol," *Br. J. Obstet. Gyn.* 1998; 105:100–102.

*Primary Examiner*—Zohreh Fay
*Attorney, Agent, or Firm*—Shanks & Herbert

[57] ABSTRACT

A topical drug application for the alleviation of keratoconjunctivitis sicca (dry eye syndrome) is comprised of a solution of 17-β-estradiol suspended or dissolved in a vehicle, and the method of preparation and application of the same. In the preferred embodiments, 17-β-estradiol is in a lipid vehicle or 17-β-estradiol 3-phosphate disodium dissolved in an aqueous vehicle having a pH of between about 6 to about 8. This invention may also be useful in treating other conditions where KCS may occur, such as postoperative corneal transplant patients and patients who cannot receive replacement estrogen therapy.

32 Claims, 5 Drawing Sheets

DRUGS FOR TOPICAL APPLICATION OF SEX STEROIDS IN THE TREATMENT OF DRY EYE SYNDROME, AND METHODS OF PREPARATION AND APPLICATION

TECHNICAL FIELD AND INDUSTRIAL APPLICABILITY

This invention relates to the topical application of sex steroids in the treatment of human dry eye syndrome (also known as keratoconjunctivitis sicca (KCS)) and, more specifically, to the preparation and application of 17-β-estradiol and its derivatives in lipid, liposomes, polymers, or aqueous or non-aqueous vehicles for the topical treatment of the ocular surface tissues. This invention may also be useful in treating other conditions where KCS may occur, such as post-operative corneal transplant patients.

BACKGROUND

The high incidence of keratoconjunctivitis sicca in the population of postmenopausal women is attended by symptoms ranging from mild foreign body sensation to frank pain and visual loss due to ocular surface abnormalities.

The standard treatment with artificial lubricants, which provides temporary symptomatic relief in most cases does not, however, address the cause of the dry eyes. While there has been described treatment of post menopausal females with dry eye syndrome using oral Premarin therapy, the oral or parenteral administration of estrogen can frequently produce side effects such as vaginal bleeding, breast tenderness and other undesired effects and the therapeutic effects derived from oral therapy are minimal. This result is now understood as a result of studies showing that there are very few estrogen receptors in the conjunctiva relative to other tissues of the body (Gans, L. A., et al., Am. J. Ophthalmol. 109(4):474–477 (1990)). Further, such oral or parenteral administration implicates the entire body structure in an indeterminate effort to secure an effect in a localized area (the eye), in the absence of any data relating the level of estrogen introduced into the blood stream to the level, if any, resulting in the tear fluid (it is known generally, that estrogen concentrations in the eye to be in the range of about 10% of serum levels). Conservative medicine would indicate the desirability of limiting the specific effect of the hormone to the recipient site if possible. One possible method of accomplishing this is through the use of topically applied steroids, in drop form. One early reference (Bohigian, G. Handbook of External Diseases of the Eye (Alcon, Inc.) 1980, p. 79) did refer to the use of "special drops" for treating KCS which in fact, contained conjugated estrogens, however, in a declaration during prosecution of U.S. Pat. No. 5,041,434 issued to Lubkin (reissued as U.S. Pat. No. Re. 34,578) and hereby incorporated by reference, Dr. Bohigian stated that the concentration of estrone in the drops was 0.0066% by weight and that it was not effective in alleviating any symptoms. In contrast, the U.S. Pat. No. Re. 34,578 patent of Lubkin showed that treatment of dry eye syndrome or KCS was shown to be effective using a form of estrogen in solution at concentrations of at least 0.1 mg/mL or 0.1% (w/v).

Further studies since about 1990 have shown that estrogen is a component of human tears and that it may play a role in ophthalmic changes in ocular tissue (Kramer, P. et al., Ophthalmol. 1990 97:303–307; Metka, M. et al., Maturitas1991 14:3–8). Other studies, even more recently, have intimated that post-menopausal patients given low systemic doses of estriol (a hydroxylated form of 17-β-estradiol) at a dose of 0.25 mg per day, or that even near homeopathic concentrations of 17-β-estradiol (0.00025%) in drops applied every 6 hours (in women already taking 2 mg estriol valerate daily by mouth) gave varying or marginal improvement in corneal lens transmittance and autofluorescence (Benitez de Castillo, et al., Ophthalmol. 1997 104:970–973).

While it has been shown in the U.S. Pat. No. Re. 34,578 patent that eye drops with concentrations of 17-β-estradiol in solution of at least 0.1% or greater are effective in treating the symptoms of KCS in post-menopausal women even in the absence of concomitant oral estrogen there is currently no available treatment for KCS which uses 17-β-estradiol in solution at concentrations below 0.1%. The invention discloses that such a concentration is extremely useful medically. The present invention shows that the effective concentration of 17-β-estradiol in solution can be as low as at least 0.05% to about 0.1% and continue to be effective regardless of the presence or absence of concomitant oral estrogen therapy in post-menopausal women. This lower dose range is especially useful in providing eye drops that will contain a concentration of 17-β-estradiol that is low enough to be both safe and effective (the medical aspect) yet has the potential to be approved by the FDA for use in non-prescription (OTC) based formulations (the commercial aspect). One can also significantly decrease any potential systemic absorption of estrogen from the present invention by combining the use of the drops with a punctal plug. A punctal plug is a small device which fits inside the punctum lacrimale of the eye and prevents tears from draining into the nasophayngeal cavity through the lacrimal canaliculi. The result of using such a plug is that the tears do not drain away from the corneal surface allowing a greater buildup of lacrimal fluid around the eye. Use of such a plug can either be temporary or permanent and has been used to alleviate eye dryness in patients.

Furthermore, dry-eye syndrome also manifests itself in pre-menopausal women who have hormonal abnormalities including insufficient estrogen production. Typically, these patients often present complaints to their ophthalmologists about the inability to wear contact lenses because of their extreme discomfort. Only upon further examination is the hormonal imbalance identified. The present invention is useful in treating the physical conditions described, but its use should not be considered to be limited to only those listed above.

SUMMARY OF THE INVENTION

Accordingly, it is a principal object of this invention to provide treatment by topical application of 17-β-estradiol suspended or dissolved in a suitable vehicle to the conjunctival surface of the eye to alleviate dry-eye syndrome or KCS. The illustrative vehicle comprises a lipid (oil based) suspension or an aqueous solution having a pH within the range of 4–8, preferably pH 6–8. It is contemplated that this invention can also utilize a liposomal vehicle as well. It is further contemplated that this invention can be comprised of a biologically compatible polymeric composition which can release a controlled amount of steroid over a much longer period of time than presently possible with a drop. More particularly, the object of the invention is to provide specific drug products applicable to these purposes, and the methods of preparation and application of the same. Even more particularly, the present invention can be used to treat symptoms of dry eye syndrome in post-menopausal women, women who have had oophorectomies or total hysterectomies including removal of the ovaries, and pre-menopausal women with hormonal abnormalities including insufficient estrogen production.

DETAILED DESCRIPTION AND PREFERRED EMBODIMENTS

The preferred embodiment or formulation comprised an aqueous solution of a derivative of estrogen known as 17-t-estradiol (the 3-phosphate disodium salt). The drug substance is also known as 17-$\beta$-estradio 3-phosphate disodium and 1,3,5(10)-estratriene-3,17 beta-diol 3-phosphate disodium. The formulation is $C_{18}H_{23}O_5P_1Na_2$, having a molecular weight of 396.3 (anhydrous).

Each gram of 17-$\beta$-estradiol (as the 3-phosphate disodium salt) contains approximately 687 milligram of 17-$\beta$-estradiol on an anhydrous basis. 17-$\beta$-estradiol (as the 3-phosphate disodium salt) is available from Research Plus, Inc., Bayonne, N.J. 07002 (catalog No. 1850-5). The compound is a white crystalline powder with an ill-defined melting point and purity better than 98%. The material is to be stored in sealed vials under refrigeration when not in use.

In one embodiment, it is contemplated thata sterile, ophthalmic solution of 17-$\beta$-estradiol can be comprised of a liposomal drug delivery system. Margalit R., *Crit. Rev. Ther. Drug Carrier Syst.* 1995;12(2–3):233–61. Liposomal therapy has been successfully used in ophthalmology not only for pre- and postoperative antisepsis, but also for the treatment of bacterial and viral conjunctivitis and for prophylaxis against ophthalmia neonatorum. Reimer K, et al., *Dermatology* 1997;195 Suppl. 2:93–9. A Method for formulating such a product can be found in U.S. Pat. No. 5,662,931 (Munechika, K. et al.) and herein incorporated by reference. A liposome system for delivery of 17-$\beta$-estradiol is disclosed in example 3 below.

In an alternate embodiment, a sterile, ophthalmic suspension of 17-$\beta$-estradiol cypionate is dissolved to form a 0.1% (by volume) solution in a vehicle which may in one embodiment take the form of a lipid based solution having a pH within the range of 4–8 with a preferred range of about 6–8.

In an alternate embodiment, a sterile, ophthalmic solution of 17-$\beta$-estradiol (as 3-phosphate disodium salt) is dissolved to form a 0.1% (by volume) solution in a vehicle which may in one embodiment take the form of a typical over-the-counter artificial tear solution. The concentration of 17-$\beta$-estradiol in the vehicle is in creased or decreased depending on the activity of the 17-$\beta$-estradiol (as 3-phosphate disodium salt). Below are alternate embodiments of the drops.

A. 17-$\beta$-estradiol (as the 3-phosphate disodium salt) and its water-soluble, storage-stable derivatives (beta-estradiol glucuronide, beta-estradiol hemisuccinate, beta-estradiol phosphate, beta-estradiol sulfate and their 3,17 diesters, 17 monoesters and 3 monoesters). The 17-$\beta$-estradiol 3-phosphate disodium salt is employed in the preferred embodiment because of the enhanced solubility and stability of the particular derivative at essentially neutral pH 6–8 (though the pH is not absolutely critical and could have a pH between 4–8) and the ease of sterile ophthalmic manufacture.

TABLE 1

B. The sterile ophthalmic ointment formulated to melt at body temperature containing:

| Compound | Concentration (w/v %) |
| --- | --- |
| 17-$\beta$-estradiol (microcrystalline) | 0.05–0.1 |
| propyl paraben (USP) | 0.2 |
| Anhydrous liquid lanolin | 5.0 |
| mineral oil (USP) | 10.0 |
| white petrolatum (USP) | 84.6–84.7 |

TABLE 2

C. A sterile aqueous ophthalmic suspension and formulated to contain:

| Compound | Concentration (w/v %) |
| --- | --- |
| 17-$\beta$-estradiol (microcrystalline) | 0.05–0.1 |
| polysorbate 80 (USP) | 0.2 |
| povidone (USP) (K-30 type) | 1.0 |
| hydroxyethylcellulose (USP) | 0.5 |
| sodium chloride (USP) | 0.5 |
| disodium edate (USP) | 0.05 |
| benzalkonium chloride (USP) | 0.005 |
| dil. HCl for pH adjustment | qs |
| purified water (USP) | qs |

The following is a description of the manufacturing and packaging procedure for a preferred drug product of our invention. More information on the preparation and characteristics of poly-estradiol phosphate is set forth in the article by E. Diczfalusy entitled High Molecular Weight Enzyme Inhibitors, pp. 1675–1689, Chemica Scandinavia Vol. 12 (1958) No. 8, which is incorporated herein by reference.

The method of synthesis of 17-$\beta$-estradiol 3-phosphate disodium is reported in Acta Chem. Scan. 12, 1675–1689 (1958) and is briefly described as follows:

17-$\beta$-estradiol 17-acetate (Molecular Weight=314.4, Melting Point 220–224° C. and optical rotation 47°) is phosphorylated in the presence of concentrated orthophosphoric acid ($H_3PO_4$) with heat and refluxing to yield the intermediate 17-$\beta$-estradiol 3-phosphate 17-acetate. The latter compound is selectively hydrolyzed in the presence of sodium bicarbonate in aqueous alcohol to yield sodium acetate and 17-$\beta$-estradiol 3-phosphate disodium. The desired steroid phosphate ester is recrystallized from dilute alcohol.

A complete list of components present in a preferred embodiment of the drug product in accordance with the present invention—including the drug substance, is as follows (in percentages by volume):

17-$\beta$-estradiol (as 3-phosphate disodium salt) 0.1%

The concentration in subsequent batches may be increased or decreased depending upon the activity of 17-$\beta$-estradiol (as 3-phosphate disodium salt).

The vehicle may be supplied as a typical over-the-counter artificial tear (solution) with a composition of the vehicle as follows:

TABLE 3

| Compound | Concentration |
| --- | --- |
| Povidone (USP) (K-30 type) | 1.67% by volume |
| Hydroxyethylcellulose (USP) | 0.44% by volume |
| sodium chloride (USP) | 0.6% by volume |

TABLE 3-continued

| Compound | Concentration |
| --- | --- |
| Anhydrous sodium phosphate (Na$_2$HPO4) (USP) | 0.3% by volume |
| Disodium edate (USP) | 0.1% by volume |
| dil. HCl or NaOH for pH adjustment | qs |
| purified water (USP) | qs |

The preferred drug product used in our invention is manufactured and packaged as follows:

i) A calculated amount of 17-β-estradiol (as 3-phosphate disodium salt) on an "as is basis" is weighed accurately on a suitable balance and carefully transferred to a sufficient volume of vehicle.

ii) The drug product is mixed until a clear solution of 17-β-estradiol (as 3-phosphate disodium salt) in the vehicle is obtained. (The pH of the solution may be adjusted to pH 7 with dilute hydrochloric acid (HCl) or dilute sodium hydroxide (NaOH) if required). The drug product is brought to final volume with additional vehicle and mixing.

iii) The drug product is sterile filtered using an appropriate sterile filter assembly and a suitable syringe and filled directly into previously sterilized (see iv) 7 ml No. 211632 low-density polyethylene Wheaton-style dropping bottles with a snap-tip dropper insert and polypropylene overcap (Wheaton Scientific, Millville, N.J. 08332). This portion of the operation is performed directly in front of a class 100 laminar flow unit (of the type sold by Dexon, Inc., Minneapolis, Minn.).

iv) Air blow Wheaton dropping bottles, inserts and caps are placed inside low density polyethylene sterilizing bag sold as MEDI-PLUS by (name company); and the bag and contents are sterilized in a 3M ETO sterilizer, Model No. 202BA unit for 2 hours at 60° C.

Based upon the chemistry of steroid phosphate esters, clarity of aqueous solution at essentially neutral pH values should be indicative of the presence of intact steroid phosphate ester. On the other hand, turbidity, haze formation or precipitate formation will indicate the presence of hydrolyzed, insoluble, free 17-β-estradiol.

Very small amounts of free, water-insoluble 17-β-estradiol can be tolerated in the steroid ophthalmic product as long as the homogeneity of the drug product is maintained because it is the 17-β-estradiol itself that is undergoing clinical study and not the phosphate ester pro-drug.

Solutions of drug product are preferably stored at controlled room temperature (15 to 30° C.) preferably at 22 to 24° C. as long as adequate physical stability (i.e., clarity of solution) is maintained. Otherwise storage under refrigeration (less than 10° C.) may be required.

It is also contemplated in an alternate embodiment, that the above drops use a modified preservative system as described in Table 3. More particularly, this alternate embodiment can use methyl paraben at a concentration (w/v) of about 0.05–0.5% in combination with phenoxyethanol at a concentration (w/v) of about 0.1–1.0%.

The placebo used in controlled clinical trials is the vehicle used in the manufacture of the drug product, namely a typical over-the-counter artificial tear (solution), similar to the formula of which is identified previously. The placebo is a non-prescription, over-the-counter drug product used to provide temporary relief of dry eye symptoms. It contains mucin-like substances (povidone and hydroxyethylcellulose) which mimic the action of the conjunctival mucus or render the surface of the eye more wetable. The vehicle helps keep the eye moist and assures that the tear film can spread easily and evenly over the eye surface.

The preferred vehicle for 17-β-estradiol (as 3-phosphate disodium salt) has the following attributes:

a) a sterile, buffered isotonic solution.

b) contains mucin-like substances that tend to increase the contact time between the active drug substance (17-β-estradiol (as the 3-phosphate disodium salt) and the eye surface.

c) free of benzalkonium chloride, which is a cationic surfactant that is known to be incompatible in solutions with steroid sodium phosphate salts.

The following quality control procedures are employed to assure identity, strength, quality and purity of the drug product:

Representative samples of finished drug product are opened and examined for clarity of solution (clear, colorless to pale yellow solution, essentially free of foreign matter), pH content (not less than 7 and not more than 8) and a simple potency assay (absorbance read at 280 nanometers using 1 centimeter cells in a suitable spectrophotometer after diluting the drug product with alcohol or methanol to a suitable concentration. Comparison will be made to the absorbance of a standard solution of 17-β-estradiol 3-phosphate disodium salt) is performed.

In yet an alternate embodiment, it is contemplated that the composition of said invention be free of any preservative compounds such as, for example, Thimerosal (USP) and said invention be provided to patient in a sterile single or similar package allowing no more than 3 to 5 days of use before the patient discards the package.

In an another alternate embodiment, it is contemplated that the present invention utilize an ocular insert means of delivering the 17-β-estradiol ingredients directly to the ocular surface and conjunctiva. Such delivery systems are well known in the art and are exemplified by the disclosure a patent (U.S. Pat. No. 4,478,818, Shell et al.) to Alza Corporation (Palo Alto, Calif.) and hereby incorporated by reference.

In yet another alternate embodiment, it is contemplated that the present invention utilizes a thermosetting gel with a low sol-gel transition temperature as a method of delivering the 17-β-estradiol ingredients directly to the ocular surface and conjunctiva. Such delivery systems are well known in the art and are exemplified by the disclosure a patent (U.S. Pat. No. 4,474,571, Haslam et al.) to Merck & Co., Inc. (Rahway, N.J.) and hereby incorporated by reference.

In yet another alternate embodiment, it is contemplated that the present invention utilize 17-β-estradiol as an encapsulated agent for introduction into the suprachoroid of the eye for therapeutic purposes. The administration of 17-β-estradiol can be controlled and maintained for long periods of time, while ensuring the substantial absence of significant concentrations of 17-β-estradiol outside the site of administration. Examples of such materials and techniques are shown in the various U.S. Pat. Nos. 4,853,224, 4,997,652, 5,164,188, 5,443,505, and 5,766,242 (Wong, et al.) and are hereby incorporated by reference.

The quality control procedures are also the same as for the active drug product described above with the exception that the ultraviolet absorbance at 280 panometers of the placebo solution when diluted to the same concentration as the active drug product will fail to indicate the presence of 17-β-estradiol (as the 3-phosphate disodium salt) in representative samples of the placebo solution.

EXAMPLE 1

Although the present invention has be en described with reference to several illustrative examples, it will be understood that the invention is not limited to the examples given herein by way of illustration, but only by the scope of the appended claims.

Prior to an application of a drug formulated in accordance with the present invention it was necessary to establish the presence of dry eye syndrome in the test population and to follow its course under treatment. It is imperative that the diagnosis of dry eye syndrome be correct and the patient not be suffering from other or additional ophthalmic diseases such as Sjörgen's syndrome. Most often, KCS is diagnosed by use of the Schirmer test. The Schirmer test, however, is a terribly inaccurate test. It consists of taking a strip of filter paper 30 mm long and 5 mm in length and placing it in the patient's lower conjunctival sac. After 5 minutes, the length of paper moistened is measured and used as an indicator of lacrimal fluid quantity. Factors such as temperature, humidity, lacrimal viscosity, types of filter paper used, batch variations between lots of paper, and other factors can significantly affect the data produced by this test.

The diagnosis of dry eye syndrome in the present invention, was made on the basis of the following tests. Initially, microscopic evaluation of the tear film with particular attention to the marginal tear strip, viscosity and debris content of the precorneal tear film, and lid examination is performed. This is followed by staining the ocular surface with Rose Bengal, a vital dye which indicates cellular damage, Schirmer testing, tear osmolarity, measurement of tear break-up time (TBUT), and finally, the maturation index (a Papanicolaou stained sample of conjunctival epithelium) are then performed.

The diagnosis of menopause was confirmed with follicular stimulating hormone and luteinizing hormone serum determinants. Dry eye postmenopausal females had mean $E_2$ (estradiol levels) of 3.47 picograms/milliliter. Normal postmenopausal females had mean $E_2$ (estradiol levels) of 16.05 picograms/milliliter (U.S. Pat. No. Re. 34,578, col. 2, Ln. 56–59).

In one embodiment of the invention, a topical drug product comprised a sterile solution of estradiol cypionate dissolved in a lipid (oil-based) vehicle at a concentration of 0.05 milligram/milliliter was tested for its effectiveness as a therapy for postmenopausal, dry-eye syndrome in a controlled, double-blind study. As a pilot project, the dose was changed after one week to 0.1 milligram/milliliter, and after two weeks to 1.0 milligram/milliliter, all performed as medication in one eye and placebo (medium) in the other.

Two drops given three times a day were indicated, but it was found that application may be more or less frequent. However, it was determined that other alternative pharmaceutical modes of administration may be used—such as a slow release mode, or any other topical method, and that the concentration may vary with individual response, as well as the treatment intervals and duration. Blood levels of the hormone used were also determined. A control bottle of just the aqueous vehicle was also made, using the estrogen preparation for one eye of the patient and the control vehicle for the other eye. A dosage of the drops four times a day for several weeks, during which time osmolarity and maturation indices were performed. No change was noted in the maturation index or osmolarity, thus the concentration was increased to (0.05%). After ten days of treatment, the control eye showed no change in the experimental parameters while the eye receiving topical estrogen showed epithelial maturation commonly seen during ovulation in premenopausal females.

The effectiveness of estrogen and its derivatives in treating keratoconjunctivitis sicca was confirmed by the use of an intravenous sterile solution of conjugated estrogens kept refrigerated during use. The drug remained active for 60 days when refrigerated at 4–15° C.

Blood Concentrations of Estrogen in Subjects Treated with 0.1% 17-β-estradiol

Measurements were taken which fell within a range 0 to 30 milli-International Units (m I.U.) of 17-β-estradiol.

TABLE 4

Estrogen Blood Level at 0.1% dose

| Patient No. | Estrogen Blood Level at 0.1% dose |
|---|---|
| 1 | 13 |
| 2 | 36 |
| 3 | 136 |
| 4 | 3 |
| 5 | 9 |
| 6 | 40 |
| 7 | 19 |
| 8 | 89 |
| 9 | 12 |
| 10 | 22 |
| 11 | 41 |
| 12 | 44 |

The average blood concentration of estrogen in test subjects was 15.5 m I.U. The average blood concentration of estrogen in the placebo group was 0.99 m I.U. at the beginning of the study and 7.34 m I.U. at the end of the study.

EXAMPLE 2

A phase 1 human clinical trial was conducted between November 1993 and December 1995. The objective of the present study was to evaluate the efficacy and safety of 17-β-estradiol in relieving the signs and symptoms of dry eye syndrome in postmenopausal women. 45 completed subjects were studied in the single-center, randomized, double-masked, parallel, placebo controlled study. The trial was conducted as follows:

The initial visit (Visit 1) occurred 7 days prior to the actual start of the study, where subjects were screened. Information regarding health, ophthalmic history, and patient evaluation and inclusion/exclusion based on FDA approved criteria were performed. A complete ophthalmic examination which included:

Acuity testing
Biomicroscopy
Intraocular pressure (IOP)
Ophthalmoscopy
Color vision
Tear osmolarity
Schimer's test
Tear film breakup time (tBUT)
Superficial punctate keratitis (SPK)
Rose bengal staining (RBS)

In addition, blood was drawn for FSH, LH and estradiol levels and a urine sample was collected for pregnancy testing where necessary. Subjects were given the placebo vehicle and instructed to instill the drops four times a day in both eyes for seven days. Daily diaries will be provided and subjects were given instructions on using them. They were also instructed to discontinue use 12 hours prior to the next visit and to do the same before subsequent visits.

On visit 2 (Day 1 of the study) the patient's medical history was updated and all symptoms of ocular discomfort were evaluated and recorded. The same measurements were taken as in visit 1. All those which qualified were randomized and received 0.1% estradiol, 0.25% estradiol or placebo.

The first drop of the assigned study drug or placebo was instilled in the eyes of each subject at the investigator's office. Signs or symptoms of dry eye were then evaluated by the investigator at 15, 30, and 60 minutes post-instillation. Subjects were then instructed to begin instilling the drug four times a day for a total of 90 days beginning the next day. Signs and symptoms of dry eye were evaluated by subjects immediately before the 8:00 a.m. (first) dosage and 8:00 p.m. (last) dosage of the drops.

The subjects returned for follow-up on days 14, 30 and 60. During these visits the patient's medical history was updated and all symptoms of ocular discomfort were evaluated and recorded. The same measurements were taken as in visit 2.

On the final exit visit (visit 6), the subjects stopped the treatment regimen and reverted back to their usual ocular lubricants. The same examination procedures were performed as on visit 1. All study drugs and subject daily diaries were collected and an exit form for each patient was completed for all subjects. All subjects were advised to return for a post-study follow-up on day 105 (visit 7), with the same examination procedures were performed as on visit 1.

The results of our study were most impressive. The data indicated a strong trend that estradiol drops significantly improve both hallmark symptoms and objective parameters. Graphical representations of the mean change for subjective scores, SPK, Rose Bengal, tBUT, and Osmolarity are shown in FIGS. 1 to 5, respectively. Statistically significant results were found when evaluating subjective complaints of redness and foreign body sensation amongst placebo and treatment groups. When comparing the two treatment groups combined vs. placebo, the p-values for tear break up time were 0.08 and for the subjective measures, the p-value was 0.13. When the 0.1% group was independently compared to placebo, the p-value for osmolarity came to 0.056 and for tear break up time 0.066.

Forty four of forty five patients completed the entire study. Although the study size is limited (due to severe inclusion/exclusion criteria) and provides us with only a 40% chance of finding a moderate to large clinical effect at a p=0.05, several findings stand out. If one looks at the means of the differences for all groups (placebo, 0.1% Estradiol, 0.25% Estradiol, the mean difference in the score between the second and sixth visits (T6–T2) for all subjective (FIG. 1) and objective outcome' variables), several of the measures (tear break up time (FIG. 4), Rose Bengal (FIG. 3), Osmolarity (FIG. 5), the sum of the subjective measures) deviate in the hypothesized direction. For example, the means for tear break up time decrease with increasing dosage. The second and sixth visits were used because the study medication was started on visit 2 and stopped at visit 6.

A Wilcoxon Rank Sum Test on the 0.1% group was independently compared with the placebo group on all clinical and subjective measures (table 5). As this data was normally distributed, t-tests were used to assess if the means of the variables differed.

TABLE 5

Analysis Of Mean Differences Between Placebo And 0.10% Estradiol Treatment

| Test | N value | P-value |
|---|---|---|
| Osmolarity | | 0.056 |
| Placebo | 12 | |
| 0.10% | 18 | |
| tBUT | | 0.066 |
| Placebo | 12 | |
| 0.10% | 18 | |
| Subjective | | 0.17 |
| Placebo | 12 | |
| 0.10% | 18 | |
| Rose Bengal | | 0.17 |
| Placebo | 12 | |
| 0.10% | 18 | |
| SPK | | 0.72 |
| Placebo | 12 | |
| 0.10% | 18 | |
| Schirmer's | | 0.82 |
| Placebo | 12 | |
| 0.10% | 18 | |

Figure 1:
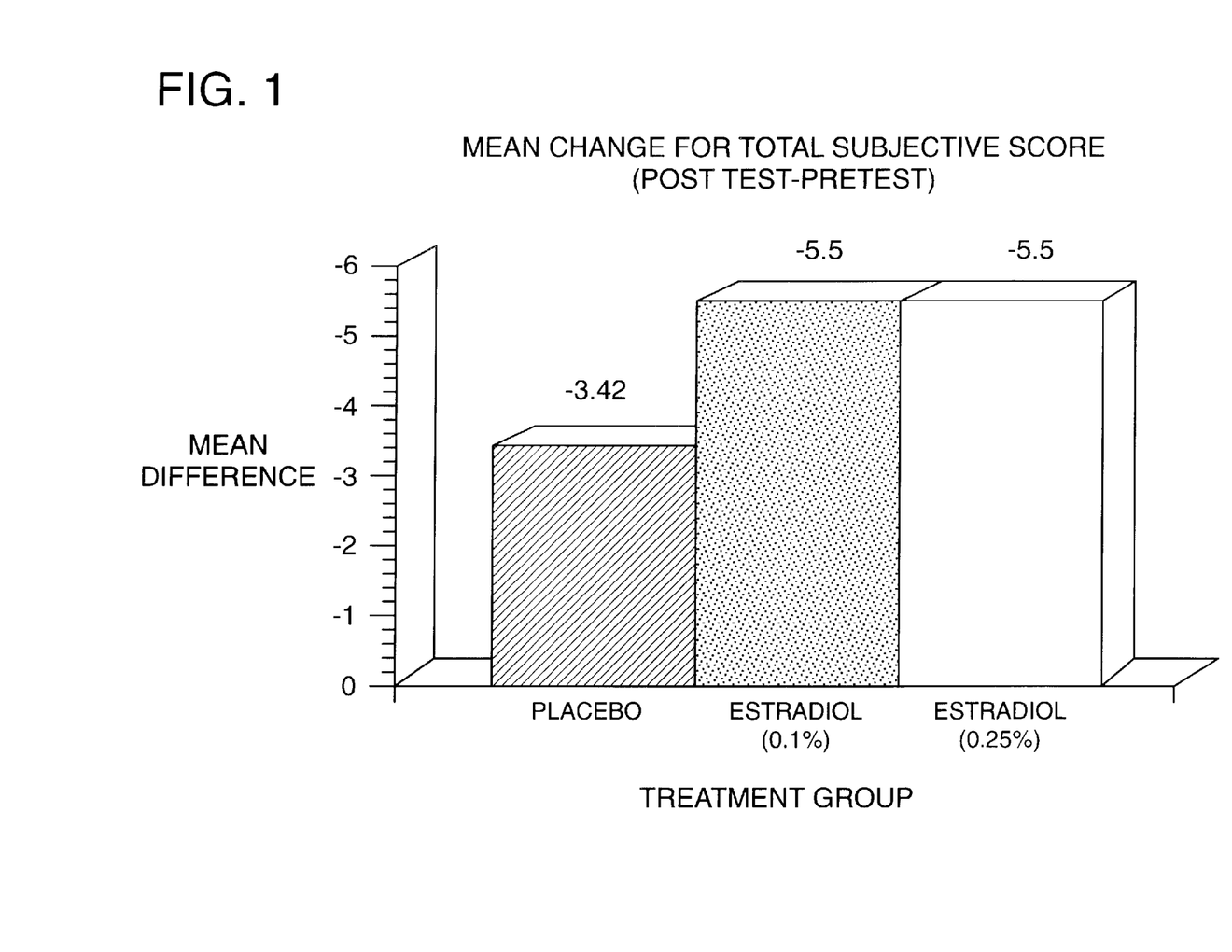
FIG. 1 shows the mean change for total subject scores of the test.
Figure 2:
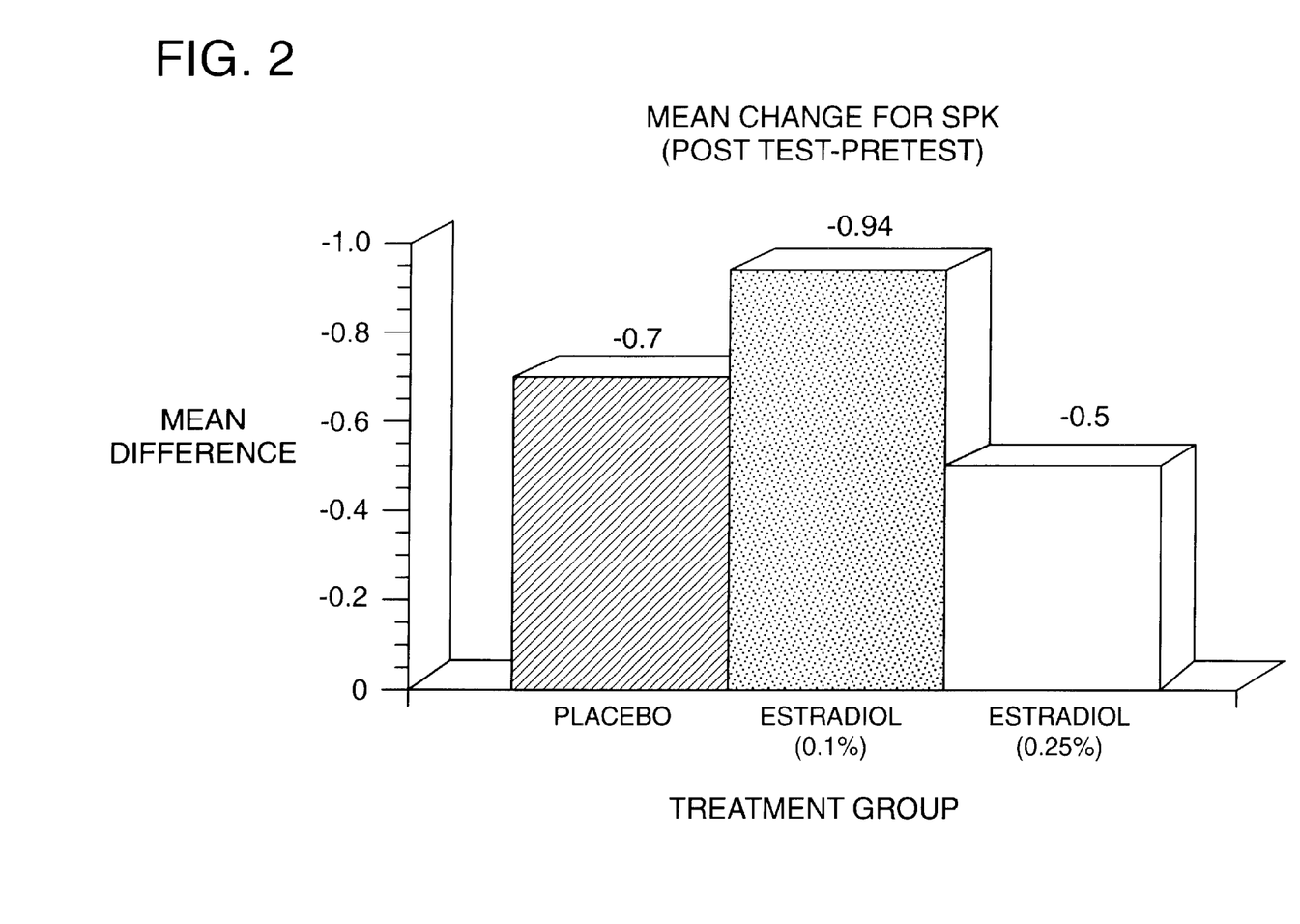
FIG. 2 shows the mean change for SPK testing.
Figure 3:
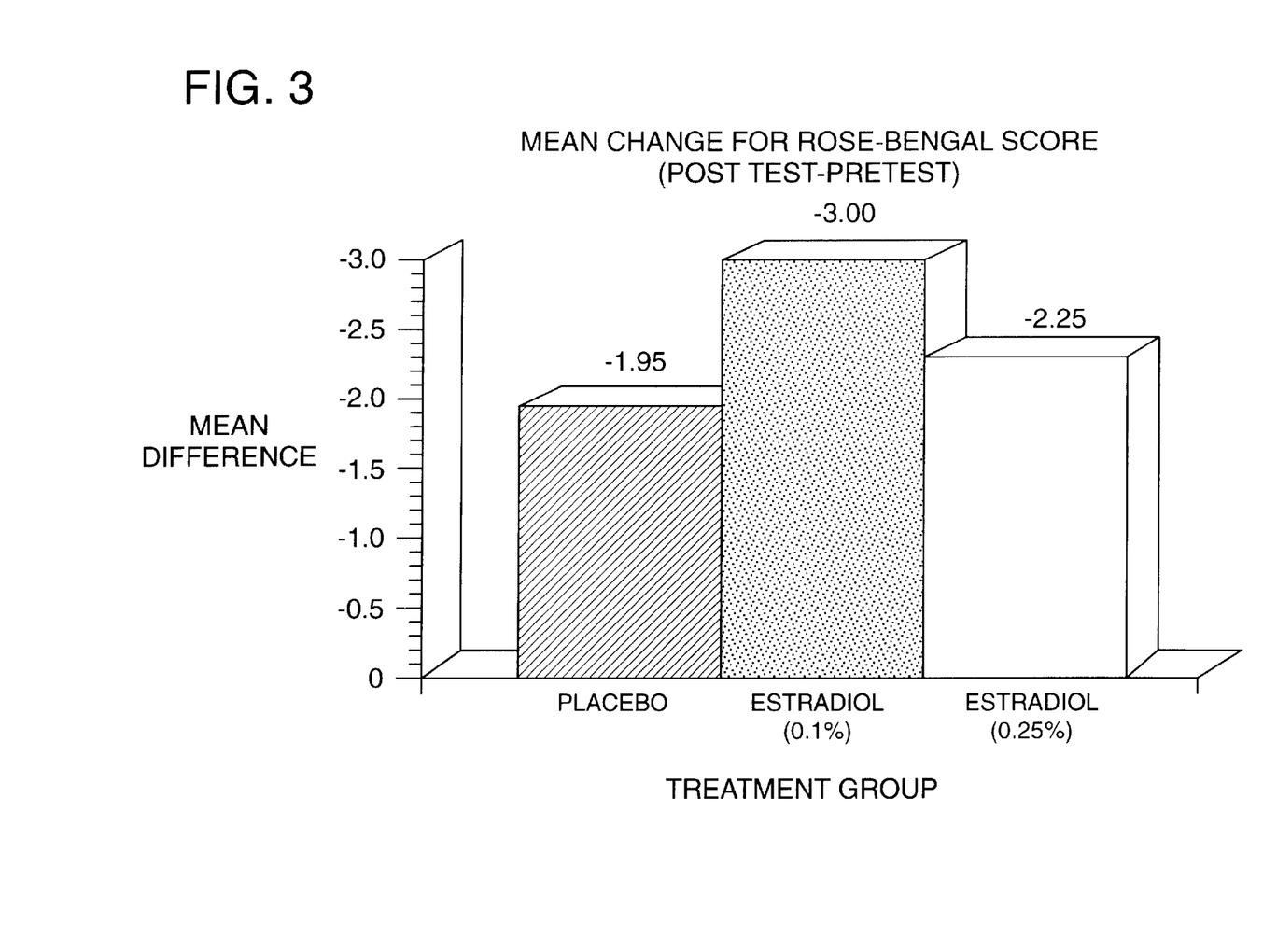
FIG. 3 shows the mean change for the Rose-Bengal testing.
Figure 4:
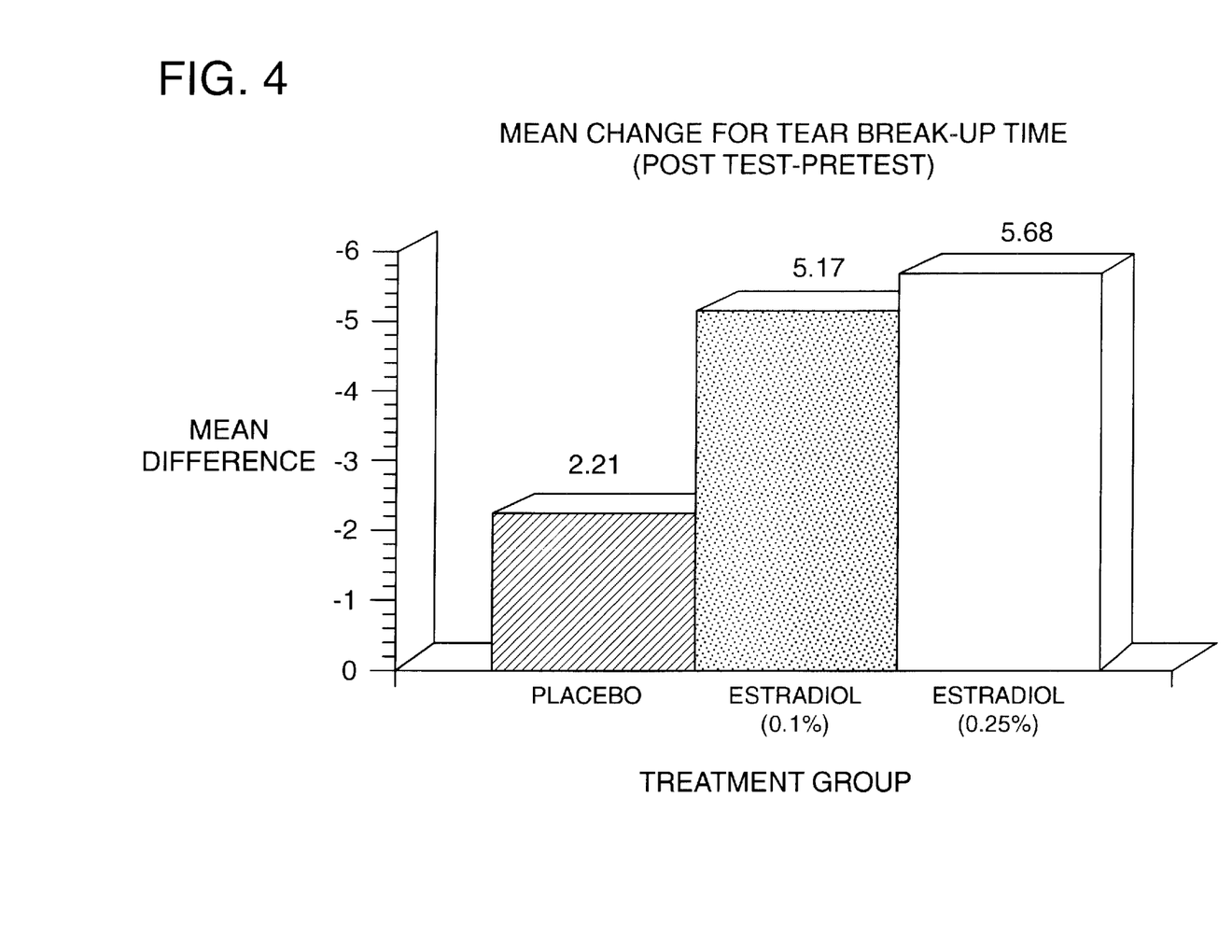
FIG. 4 shows the mean change for the tBUT testing.
Figure 5:
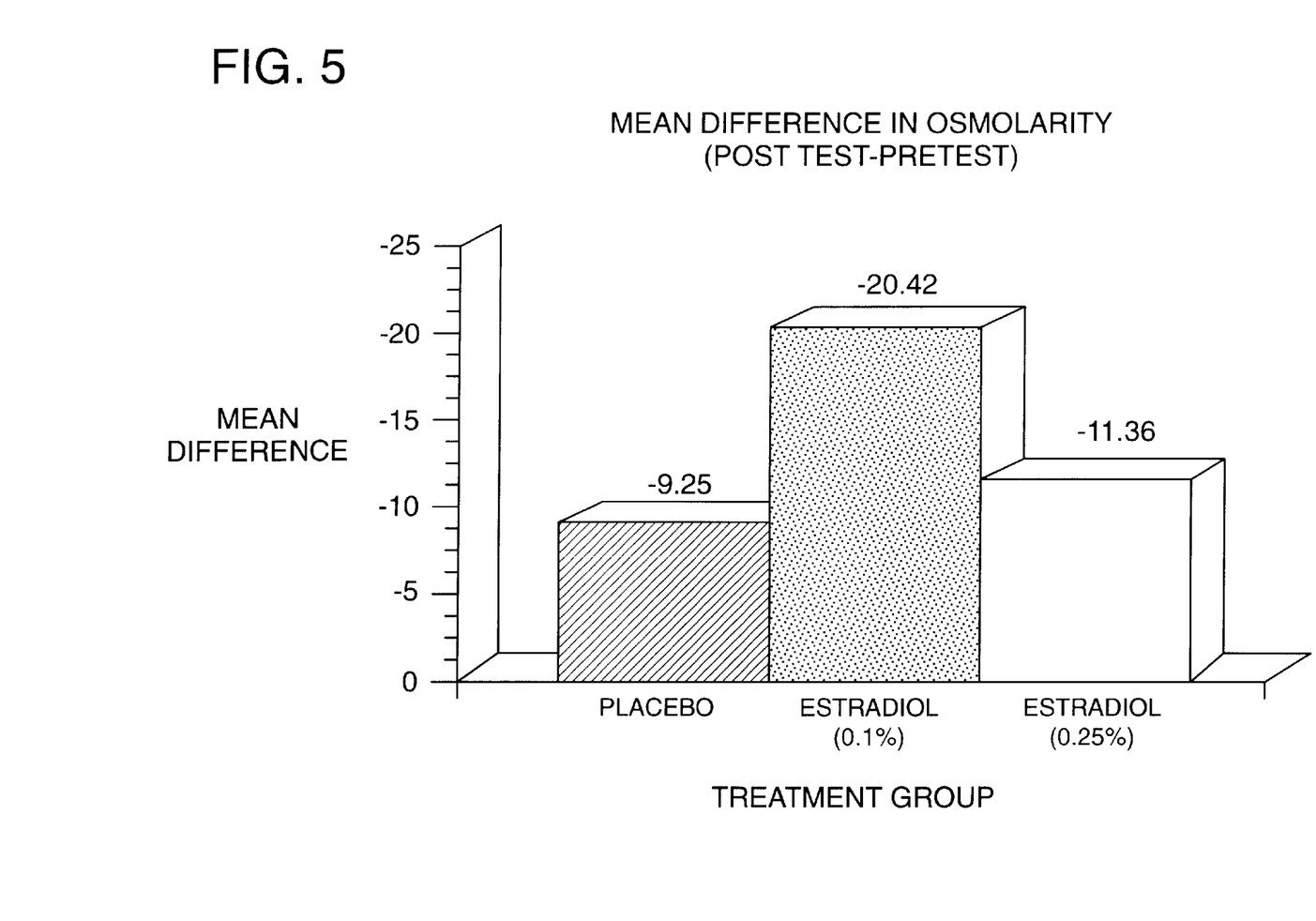
FIG. 5 shows the mean change for Osmolarity.

Finally, an analysis of the individual subjective ratings was performed (FIG. 1). Three tests were conducted. First, an overall test looked for differences in the distribution of scores among the three groups without regard to level. Differences between the 0.1% group and the placebo group were then tested (table 6). Two ratings emerged as significant at a p-level of less than 0.05: foreign body sensation and redness. For both ratings, the treatment groups showed significantly more improvement than the placebo group

TABLE 6

Analysis of Subjective Scores of Placebo v. 0.10% Estradiol

| Test | Wilcoxon values |
|---|---|
| FBS | 0.044* |
| Redness | 0.013* |
| Itching | 0.20 |
| Burning | 0.85 |

*indicates that the results were statistically significant.

The FDA found that the results of the study succeeded in its purpose in demonstrating the effectiveness of estrogen eye drops in the postmenopausal dry eye and approved advancing the study to a phase 3 trial involving two formal clinical trials in two separate centers using the final formulation.

EXAMPLE 3

A liposome delivery vehicle is shown in the table below.

TABLE 7

A Liposome Delivery Vehicle

| Ingredient | Amount (w/v %) |
|---|---|
| 17-β-estradiol | Desired amount |
| Phosphotidylcholine | 3.0 |
| Phosphotidylserine | 3.0 |
| Carbomer (N.F.) | q.s. |
| Propylene glycol | 6.0 |
| $C_{12-15}$ benzoate | 2.0 |
| Emulsifying wax | 2.0 |
| Aminomethyl propanol | q.s. |

TABLE 7-continued

A Liposome Delivery Vehicle

| Ingredient | Amount (w/v %) |
|---|---|
| Preservative (optional) | 1.0 |
| Purified water (U.S.P.) | q.s. |

Disperse the carbomer (a polymer of acrylic acid used in pharmaceutical preparations) in a portion of the purified water and heat to about 70° C. Add the 17-β-estradiol in the emulsifying wax, $C_{12-15}$ benzoate, both phospholipid derivatives and propylene glycol to about 70° C. Cool the solution to about 40° C. and adjust the pH of the solution to about pH 6.0 with the aminomethyl propanol. Add the preservative (if any) and add additional purified water to the final desired volume. While warm, filter under pressure through 0.2 μM membrane filter to form a sterile solution. Note that this method is described for example purposes and is not intended to show the only method that is possible.

What is claimed is:

1. A method of treating Dry Eye Syndrome in postmenopausal, oophorectomized or hysterectomized women comprising:

topically applying to the ocular surface and/or conjunctival tissue in said women the drug comprising 17-β-estradiol or its derivatives having a concentration range of at least 0.05% to less than 0.1% weight percent dissolved or suspended in a pharmaceutically acceptable vehicle.

2. The method of claim 1 wherein said concentration range of 17-β-estradiol or its derivatives is 0.06% to about 0.9% weight percent dissolved or suspended in a pharmaceutically acceptable vehicle.

3. The method of claim 1 wherein said concentration range of 17-β-estradiol or its derivatives is 0.075% to about 0.09% weight percent dissolved or suspended in a pharmaceutically acceptable vehicle.

4. The method of claim 1 wherein said 17-β-estradiol derivative is dissolved or suspended in a lipid vehicle.

5. The method of claim 1 wherein said 17-β-estradiol derivative is a water soluble ester and the vehicle in which it is applied consists essentially of an aqueous solution having a pH within the range of about 4 to about 8.

6. The method of claim 1 wherein said 17-β-estradiol derivative is a water soluble ester and the vehicle in which is applied consists essentially of an aqueous solution having a pH within the range of about 6 to about 8.

7. The method of claim 1 wherein said derivative comprises the 3-phosphate disodium salt of 17-β-estradiol.

8. The method of claim 5 wherein said steroid is dissolved in a vehicle consisting essentially of the composition of the human tear.

9. The method of claim 5 wherein said steroid or derivative is dissolved in a vehicle consisting essentially of the following components, of which the amounts are indicated in percentages by volume:

| Compound | Concentration |
|---|---|
| povidone (USP) (K-30 type) | 1.67% by volume |
| hydroxyethylcellulose (USP) | 0.44% by volume |
| sodium chloride (USP) | 0.6% by volume |

-continued

| Compound | Concentration |
|---|---|
| anhydrous sodium phosphate ($Na_2HPO4$) (USP) | 0.3% by volume |
| disodium edate (USP) | 0.1% by volume |
| Thimerosal (USP) | 0.004% by volume |
| dil. HCl or NaOH for pH adjustment | qs |
| purified water (USP) | qs. |

10. The method of claim 8 wherein said steroid or derivative is dissolved in a vehicle consisting essentially of the following components, of which the amounts are indicated in percentages by volume:

| Compound | Concentration |
|---|---|
| povidone (USP) (K-30 type) | 1.67% by volume |
| hydroxyethylcellulose (USP) | 0.44% by volume |
| sodium chloride (USP) | 0.6% by volume |
| anhydrous sodium phosphate ($Na_2HPO4$) (USP) | 0.3% by volume |
| methyl paraben (USP) | 0.2% by volume |
| phenoxyethanol (USP) | 0.5% by volume |
| disodium edate (USP) | 0.1% by volume |
| dil. HCl or NaOH for pH adjustment | qs |
| purified water (USP) | qs. |

11. The method of claim 8 wherein said steroid or derivative is dissolved in a vehicle consisting essentially of the following components, of which the amounts are indicated in percentages by volume:

| Compound | Concentration |
|---|---|
| povidone (USP) (K-30 type) | 1.67% by volume |
| hydroxyethylcellulose (USP) | 0.44% by volume |
| sodium chloride (USP) | 0.6% by volume |
| anhydrous sodium phosphate ($Na_2HPO4$) (USP) | 0.3% by volume |
| disodium edate (USP) | 0.1% by volume |
| dil. HCl or NaOH for pH adjustment | qs |
| purified water (USP) | qs | and said steroid or derivative is contained within a sterile delivery system such that it can only be used to deliver said steroid or derivative to the ocular surface no more than five consecutive days.

12. A method of treating Dry Eye Syndrome in female post-operative corneal transplant patients comprising:

topically applying to the ocular surface and conjunctival tissue in said women the drug comprising 17-β-estradiol or its derivatives having a concentration range of at least about 0.05% to less than 0.1% weight percent dissolved or suspended in a pharmaceutically acceptable vehicle.

13. A composition comprising:

17-β-estradiol or its derivatives having a concentration range of at least about 0.05% to less than 0.1% weight percent dissolved or suspended in a pharmaceutically acceptable liposomal vehicle.

14. A method of making the composition of claim 13, comprising 17-β-estradiol or its derivatives are dissolved in a vehicle consisting essentially of the following components, of which the amounts are indicated in percentages by volume:

| Ingredient | Amount (w/v %) |
|---|---|
| 17-β-estradiol | Desired amount |
| Phosphotidylcholine | 3.0 |
| Phosphotidylserine | 3.0 |
| Carbomer (N.F.) | q.s. |
| Propylene glycol | 6.0 |
| $C_{12-15}$ benzoate | 2.0 |
| Emulsifying wax | 2.0 |
| Aminomethyl propanol | q.s. |
| Preservative (optional) | 1.0 |
| Purified water (U.S.P.) | q.s. |

And wherein said method comprises the steps of:
a) disperse the carbomer (a polymer of acrylic acid used in pharmaceutical preparations) in a portion of the purified water and heat to about 70° C.;
b) 17-β-estradiol or a derivative, emulsifying wax, $C_{12-15}$ benzoate, both phospholipid derivatives and propylene glycol, is added into the said carbomer/water mixture, and the temperature is held to about 70° C.;
c) said mixture is thoroughly mixed, the solution is cooled to about 40° C., and the pH of the solution adjusted to about pH 6.0 with the aminomethyl propanol;
d) a preservative (if any) and add additional purified water is added to the solution to make the final desired volume; and
e) the solution is filtered through 0.2 μM membrane filter to form a sterile solution.

15. A method of treating Dry Eye Syndrome in postmenopausal, oophorectomized or hysterectomized women comprising:
topically applying to the ocular surface and conjunctival tissue in said women the composition of claim 14.

16. A method of treating Dry Eye Syndrome in postmenopausal, oophorectomized or hysterectomized women comprising:
topically applying to the ocular surface or conjunctival tissue in said women 17-β-estradiol or its derivatives having a concentration range of at least about 0.05% to less than 0.1% weight percent dissolved or suspended in a polymeric composition biologically compatible with the eye.

17. The method of claim 16 wherein said polymeric composition is comprised of a thermosetting gel wherein the sol-gel transition temperature of said polymeric composition is room temperature or below and said polymeric composition is liquid at this temperature.

18. The method of claim 17 wherein said polymeric composition comprises a biodegradable controlled-release polymer.

19. A method of treating Dry Eye Syndrome in premenopausal women having hormonal abnormalities causing insufficient estrogen production comprising:
topically applying to the ocular surface and conjunctival tissue in said women the drug comprising 17-β-estradiol or its derivatives having a concentration range of at least about 0.05% to less than 0.1% weight percent dissolved or suspended in a pharmaceutically acceptable vehicle.

20. The method of claim 19 wherein said concentration range of 17-β-estradiol or its derivatives is 0.06% to about 0.9% weight percent dissolved or suspended in a pharmaceutically acceptable vehicle.

21. The method of claim 19 wherein said concentration range of 17-β-estradiol or its derivatives is 0.075% to about 0.9% weight percent dissolved or suspended in a pharmaceutically acceptable vehicle.

22. The method of claim 19 wherein said 17-β-estradiol derivative is dissolved or suspended in a lipid vehicle.

23. The method of claim 19 wherein said 17-β-estradiol derivative is a water soluble ester and the vehicle in which is applied consists essentially of an aqueous solution having a pH within the range of about 4 to about 8.

24. The method of claim 19 wherein said 17-β-estradiol derivative is a water soluble ester and the vehicle in which is applied consists essentially of an aqueous solution having a pH within the range of about 6 to about 8.

25. The method of claim 19 wherein said derivative comprises the 3-phosphate disodium salt of 17-β-estradiol.

26. The method of claim 23 wherein said steroid is dissolved in a vehicle consisting essentially of the composition of the human tear.

27. The method of claim 23 wherein said steroid or derivative is dissolved in a vehicle consisting essentially of the following components, of which the amounts are indicated in percentages by volume:

| Compound | Concentration |
|---|---|
| povidone (USP) (K-30 type) | 1.67% by volume |
| hydroxyethylcellulose (USP) | 0.44% by volume |
| sodium chloride (USP) | 0.6% by volume |
| anhydrous sodium phosphate ($Na_2HPO4$) (USP) | 0.3% by volume |
| disodium edate (USP) | 0.1% by volume |
| Thimerosal (USP) | 0.004% by volume |
| dil. HCl or NaOH for pH adjustment | qs |
| purified water (USP) | qs. |

28. The method of claim 26 wherein said steroid or derivative is dissolved in a vehicle consisting essentially of the following components, of which the amounts are indicated in percentages by volume:

| Compound | Concentration |
|---|---|
| povidone (USP) (K-30 type) | 1.67% by volume |
| hydroxyethylcellulose (USP) | 0.44% by volume |
| sodium chloride (USP) | 0.6% by volume |
| anhydrous sodium phosphate ($Na_2HPO4$) (USP) | 0.3% by volume |
| methyl paraben (USP) | 0.2% by volume |
| phenoxyethanol (USP) | 0.5% by volume |
| disodium edate (USP) | 0.1% by volume |
| dil. HCl or NaOH for pH adjustment | qs |
| purified water (USP) | qs. |

29. The method of claim 26 wherein said steroid or derivative is dissolved in a vehicle consisting essentially of the following components, of which the amounts are indicated in percentages by volume:

| Compound | Concentration |
|---|---|
| povidone (USP) (K-30 type) | 1.67% by volume |
| hydroxyethylcellulose (USP) | 0.44% by volume |
| sodium chloride (USP) | 0.6% by volume |
| anhydrous sodium phosphate ($Na_2HPO4$) (USP) | 0.3% by volume |
| disodium edate (USP) | 0.1% by volume |

-continued

| Compound | Concentration |
|---|---|
| dil. HCI or NaOH for pH adjustment | qs |
| purified water (USP) | qs | and said steroid or derivative is contained within a sterile delivery system such that it can only be used to deliver said steroid or derivative to the ocular surface no more than five consecutive days.

30. A method of treating Dry Eye Syndrome in pre-menopausal women having hormonal abnormalities causing insufficient estrogen production comprising:

topically applying to the ocular surface or conjunctival tissue in said women 17-β-estradiol or its derivatives having a concentration range of at least about 0.05% to less than 0.1% weight percent dissolved or suspended in a polymeric composition biologically compatible with the eye.

31. The method of claim 30 wherein said polymeric composition is comprised of a thermosetting gel wherein the sol-gel transition temperature of said polymeric composition is room temperature or below and said polymeric composition is liquid at this temperature.

32. The method of claim 30 wherein said polymeric composition comprises a biodegradable controlled-release polymer.

* * * * *